United States Patent [19]

Nogami et al.

[11] Patent Number: 5,500,536
[45] Date of Patent: Mar. 19, 1996

[54] SPECTROFLUOROMETER

[75] Inventors: Taro Nogami, Katsuta; Shunichi Matsuura, Ibaraki; Akira Kuroda, Mito, all of Japan

[73] Assignee: Hitachi, Ltd., Tokyo, Japan

[21] Appl. No.: 215,233

[22] Filed: Mar. 21, 1994

[30] Foreign Application Priority Data

Mar. 22, 1993 [JP] Japan ............................. 5-061580

[51] Int. Cl.⁶ ............................................ G01N 21/01
[52] U.S. Cl. ................................. 250/458.1; 356/246
[58] Field of Search ........................ 250/458.1, 459.1, 250/461.1, 461.2; 356/246

[56] References Cited

U.S. PATENT DOCUMENTS 2,549,574  4/1951  Condiff ................................. 356/246
3,518,009  6/1970  Shamos et al. ......................... 356/246

FOREIGN PATENT DOCUMENTS 60-78334  5/1985  Japan .

Primary Examiner—Davis L. Willis
Assistant Examiner—Richard Hanig
Attorney, Agent, or Firm—Kenyon & Kenyon

[57] ABSTRACT

A fluorescence output port sandwiched between light-shielding members of a sample cell is provided at a position corresponding to an entrance slit of a fluorescence monochromator and an excitation light side port of the sample cell is provided at a position corresponding to an exit slit of an excitation side monochromator.

17 Claims, 9 Drawing Sheets

EFFCTIVE FLUORESCENCE GENERATING PORTION

SPECTROFLUOROMETER

BACKGROUND OF THE DISCLOSURE

1. Field of the Invention

This invention relates to a spectrofluorometer, and in particular that suitable to measure fluorescence of a small quantity of substances contained in a liquid.

2. Description of the Prior Art

In the prior art, a spectrofluorometer comprises mainly a light source to generate excitation light, an excitation side monochromator, a specimen cell to hold a specimen to be measured, an optical detector to detect the fluorescence emitted from the said specimen and a fluorescence side monochromator.

Japanese Patent Application Laid-Open No.78334/1985 (hereafter to be referred to as the prior art) discloses an invention related to the specimen cell to hold a specimen, selected from among the said items. According to the prior art, the light generated by a light source in an excitation light side optical system is passed through an entrance slit, a concave diffraction grating, and an exit slit to obtain excitation light. The sample held in the sample cell is irradiated by the excitation light. Then, the fluorescence emitted from the sample during the irradiation is passed through the concave diffraction grating and the exit slit provided in the fluorescence grating and the exit slit provided in the fluorescence side optical system and detected by a photoelectric detector. The transitional status of the elements contained in the sample can thus be detected and a quantitative analysis is carried out for the elements on the basis of the fluorescence strength.

In the prior art, the sample cell is a container made of opaque and transparent members to form a sample chamber having its bottom. The sample chamber can limit the quantity of the light made incident thereon with the opaque member as needed.

Said prior art is effective to measure a very small quantity of specimen in fluorescence photometry, but it has the following weak points.

Conventional spectrometric devices including those mentioned in the said prior art adopt a system that condenses the fluorescence emitted from the specimen cell once using a convergence lens, then selects only the light with necessary wavelength by the fluorescence side monochromator. For general optical measuring instruments used today, it is well known that the less the number of the optical elements up to the photoelectric detector is and the less the light scattering and loss are, the higher the measuring accuracy is. However, the number of the optical elements cannot be reduced any more as long as the system in the prior art is adopted.

The optical slit itself also has a defect that the fluorescence emitted from the specimen and condensed by a lens overflows when the excitation light enters the sample cell or when the fluorescence is extracted from the sample cell. In addition, the quantity of the light is also reduced on the basis of the attenuation and reflection of the light by the convergence lenses used to pass fluorescence through the slit.

SUMMARY OF THE INVENTION

An object of this invention is to provide a spectrofluorometer capable of measuring with high sensitivity a very small quantity of substances contained in the specimen even when the optical system in the optical system can be simplified in mechanism.

In order to attain the object of this invention, a spectrofluorometer is provided which comprises a sample cell equipped with a sample chamber to hold a sample, an excitation light port to direct excitation light to said sample chamber, a fluorescence output port to derive fluorescence emitted from the sample in the said sample chamber, and light-shielding members arranged to sandwich said excitation light port and said fluorescent output port therebetween; an excitation side monochromator to derive the excitation light to be directed to said sample; a fluorescence side monochromator to disperse the fluorescence from said sample cell; and a fluorescence detector to detect the fluorescence from said fluorescence side monochromator; said sample cell being arranged so that said fluorescence output port is provided at a position corresponding to an entrance slit of said fluorescence side monochromator.

The sample cell may be arranged so that said excitation light port may be provided at a position corresponding to an exit slit of said fluorescence side monochromator.

The sample cell may be arranged so that said excitation light port is provided at a position corresponding to the exit slit of said excitation side monochromator and said fluorescence output port is provided at a position corresponding to the entrance slit of said fluorescence side monochromator.

The fluorescence output port of the sample cell may be provided at a position corresponding to the entrance slit of the conventional fluorescence side monochromator so as to be sandwiched between said light-shielding members, so that the fluorescence output port is also used as an entrance slit. Therefore, the entrance slit and the condensing lens used therefor in the prior art can be omitted.

According to the second aspect of the present invention, the excitation light port of the sample cell may be provided at a position corresponding to the exit slit of the conventional excitation side monochromator so as to be sandwiched between the light-shielding members, so that the excitation light port is also used as an exit slit. Therefore, the exit slit and the condensing lens used to make the excitation light incident on the sample cell in the prior art can be omitted.

According to the third aspect of the present invention, the excitation light port of the sample cell is provided at a position corresponding to the exit slit of the excitation monochromator so as to be sandwiched the light-shielding members and the fluorescence output port of the sample cell is provided at a position corresponding to the entrance slit of the fluorescence side monochromator so as to be sandwiched between the light-shielding members, so that those ports are also used as an exit slit and an entrance slit. Therefore, the excitation light exit slit and the fluorescence side entrance slit in the prior art in addition to the condensing lens used for both slits therein can be omitted.

These and other objects and features of the present invention will become apparent from the descriptions of preferred embodiments of the present invention taken in connection with the accompanying drawings.

DESCRIPTION OF THE PREFERRED EMBODIMENTS

Embodiments of this invention will be explained in connection with the accompanying drawings.

Figure 1:
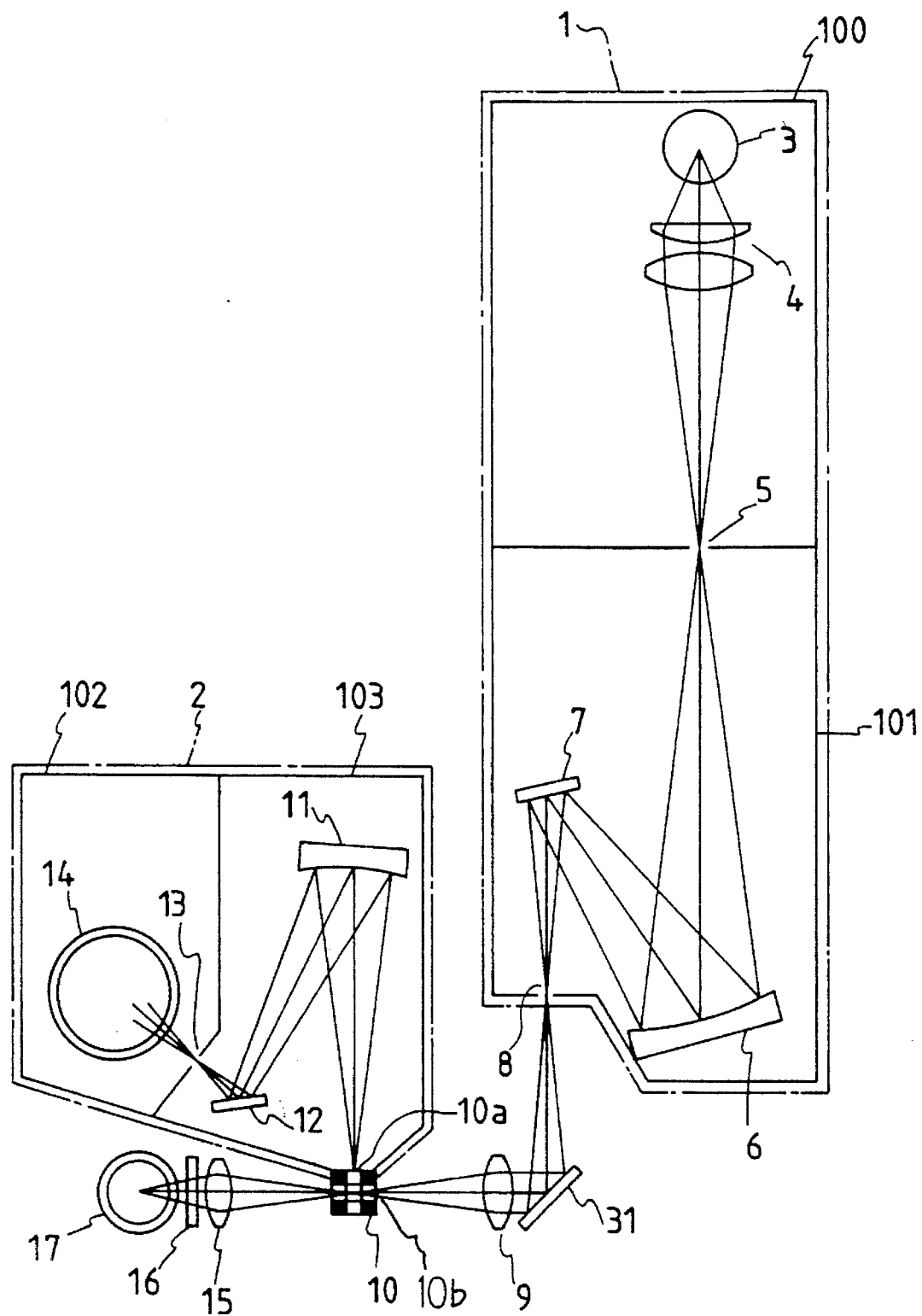
FIG. 1 is a view showing an embodiment according to the invention in a case where the fluorescence output port is arranged at a position corresponding to the fluorescence side entrance slit.
Figure 2:
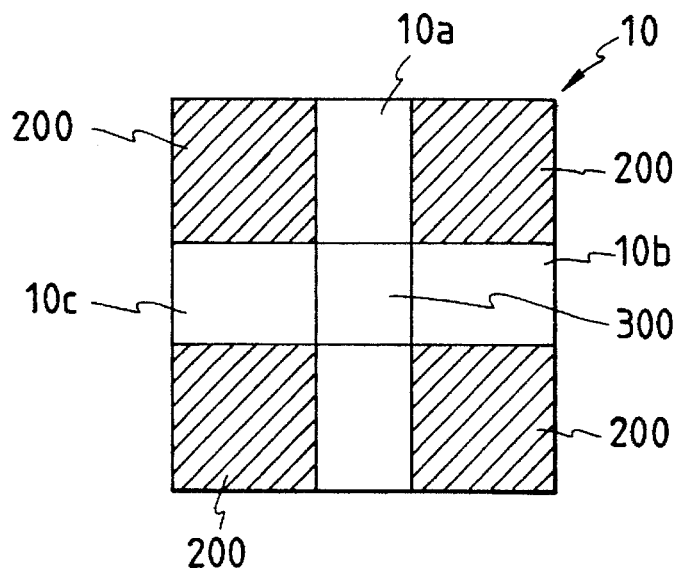
FIG. 2 is an enlarged view of the sample cell in the embodiment shown in FIG. 1.

FIG. 1 shows an embodiment in which a fluorescence output port is provided in a position corresponding to a fluorescence side entrance slit. FIG. 2 shows a cross sectional view of a specimen cell 10 adopted in FIG. 1 expanded in the horizontal direction.

The light emitted from a light source 3 disposed in a light source section 100 in the excitation side basic optical system 1 is condensed by a condensing lens 4 disposed in said light source section. The condensed light is then dispersed by a concave diffraction grating 6 in the monochromator section 101 through an entrance slit 5. The dispersed monochromatic light extracted outside the monochromator section 101 through a mirror 7 and an exit slit 8. The light path in this fig. is provided in a dark chamber and therefore the light is never affected by any light outside the system even after it is led out of the chamber. This extracted excitation light is directed to said sample chamber 300 provided in the said sample cell 10 through a mirror 31, a condensing lens 9 and an excitation light side port 10b. The specimen cell 10 is positioned so that the fluorescence output port 10a in the specimen cell 10 is arranged at a position corresponding to an entrance slit of a monochromator section 103 in a fluorescence side basic optical system 2.

Since the fluorescence output port 10a that works in the same way as an entrance slit is provided in a focusing position of a concave diffraction grating 11, the entrance slit used in the prior art is not needed any longer. In other words, the entrance slit can be removed by using the width of the fluorescence output port 10a as a pseudo slit. Thus, the light path between the sample cell 10 and the entrance slit can be omitted, as well as the condensing lens and the entrance slit in the prior art can also be omitted.

In general optical devices, it is well known that the shorter the light path is and the less the number of the components in the light path is, the smaller the measuring error to occur becomes due to the scattering and loss of the light. The system configuration of this invention is very effective to improve the measuring accuracy.

Figure 3:
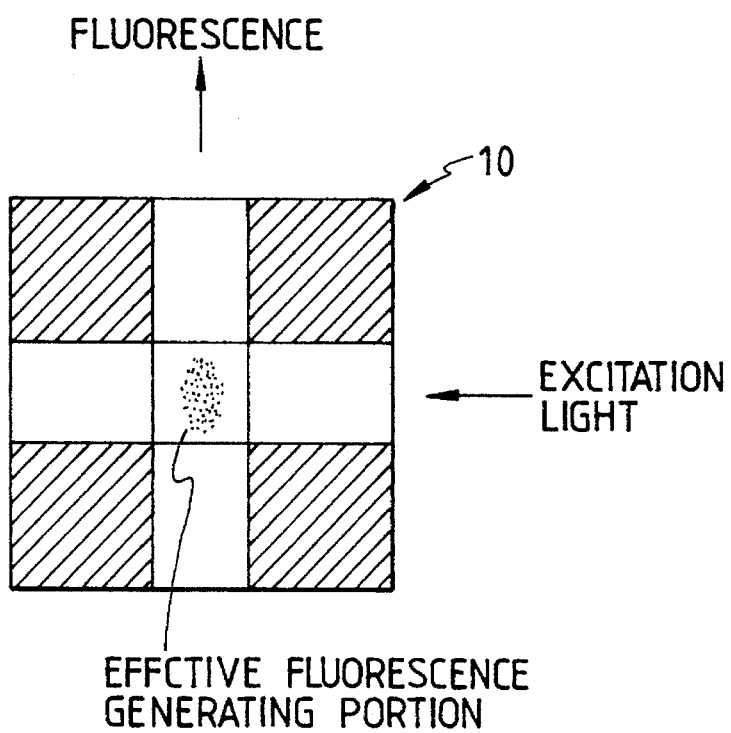
FIG. 3 is a view showing the effective fluorescence generating portion of the sample in the sample cell when this invention is not applied.
Figure 4:
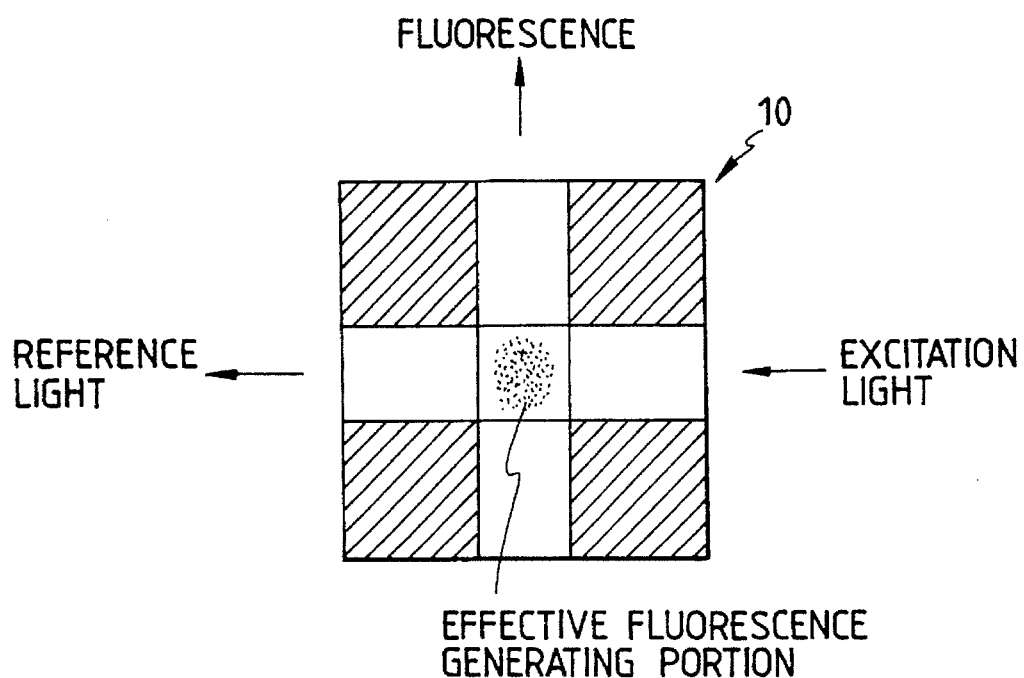
FIG. 4 is a view showing the effective fluorescence generating portion of the sample in the sample cell in the embodiment of this invention shown in FIG. 1.

Also in this embodiment, the fluorescence emitted from the fluorescence output port 10a is directly made incident on the concave diffraction grating 11. This makes it possible to eliminate the light loss to occur due to overflow light as disclosed in the prior art. This effect will be explained using FIGS. 3 and 4. FIG. 3 shows the effective fluorescence generating portion of the sample in the sample cell when the sample cell described in the embodiments of this invention is used for the spectrofluorometer in the prior art. FIG. 4 shows the effective fluorescence generating portion in the embodiment shown in FIG. 2. In FIG. 3, the effective fluorescence generating portion of the fluorescence passing through the entrance slit of the fluorescence side spectrofluorometer cannot be secured so much due to the light loss to be caused by overflowing light. On the other hand, in FIG. 4, the light loss is less, so that the effective fluorescence generating portion can be secured widely.

The fluorescence emitted from the fluorescence output port 10a is dispersed by the concave diffraction grating 11 provided in the light-separating section 103 in the fluorescence side basic optical system 2, then the fluorescence goes through a mirror 12 and a exit slit 13. The fluorescence is then measured by a photoelectric device 14 provided in the measuring section 102. Furthermore, the excitation light directed to the specimen goes out of the reference output port 10c through a condensing lens 15 and a attenuating plate 16, and detected by a reference light photoelectric device 17.

Figure 5:
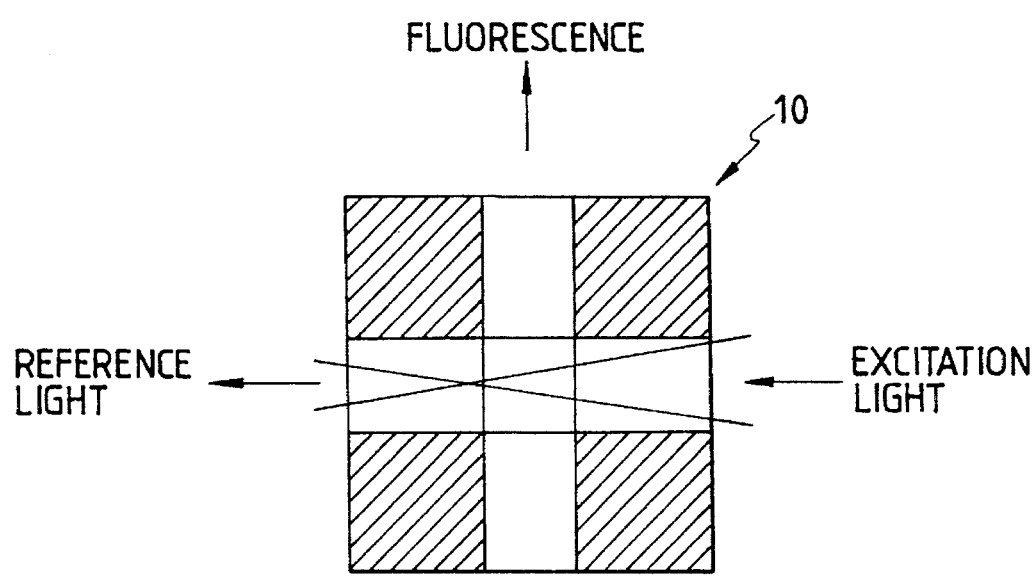
FIG. 5 is a view showing the position of the convergence of the excitation light coming into the sample cell.
Figure 6:
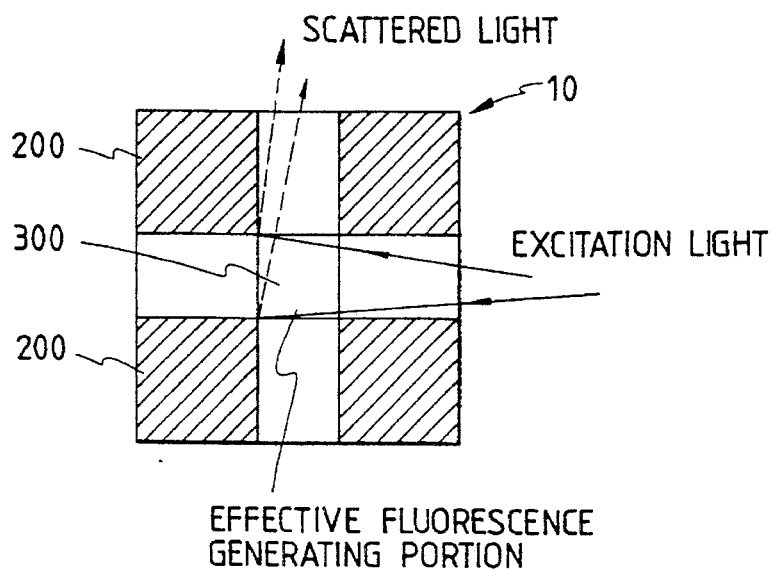
FIG. 6 is a view showing how scattered excitation light goes to the concave diffraction grating.

FIG. 5 shows the convergence position of the excitation light by which the specimen is irradiated. Affected by edges of the light-shielding members 200, the excitation light might scatter and go to the concave diffraction grating 11 as shown in FIG. 6. In this embodiment, therefore, the convergence position of the excitation light is made far from the excitation light emission side of the sample chamber as shown in FIG. 5 to solve such a problem.

Figure 7:
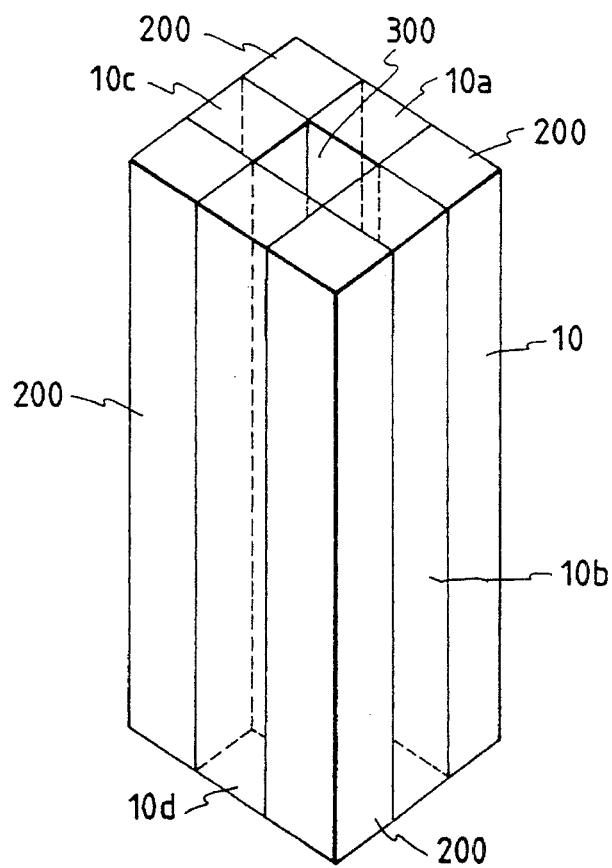
FIG. 7 is a perspective view of the specimen cell shown in FIG. 2.

The sample cell 10 used in the embodiment shown in FIG. 1 is of a flow-type and has a form as shown in FIG. 7. A light-shielding unit comprises light-shielding members 200 which are provided on the four corners in the longitudinal direction. Each of four transparent members is sandwiched between the light-shielding members 200 so that three of the four transparent members constitute the excitation light side port 10b, the fluorescence output port 10a and the reference output port 10c, respectively. The fluorescence output port 10a functions or works as an entrance slit of the monochromator section 103. The excitation light side port 10b functions as an exit slit of the monochromator section 101 in embodiments explained later in connection with FIGS. 10 and 12. The light-shielding members 200 and the transparent members constitutes the liquid-proof side walls of the sample chamber 300 so that the sample chamber 300 is made hollow through from top to bottom.

In this embodiment, black quartz is used for the light-shielding members 200, while transparent quartz is used for each port.

Figure 8:
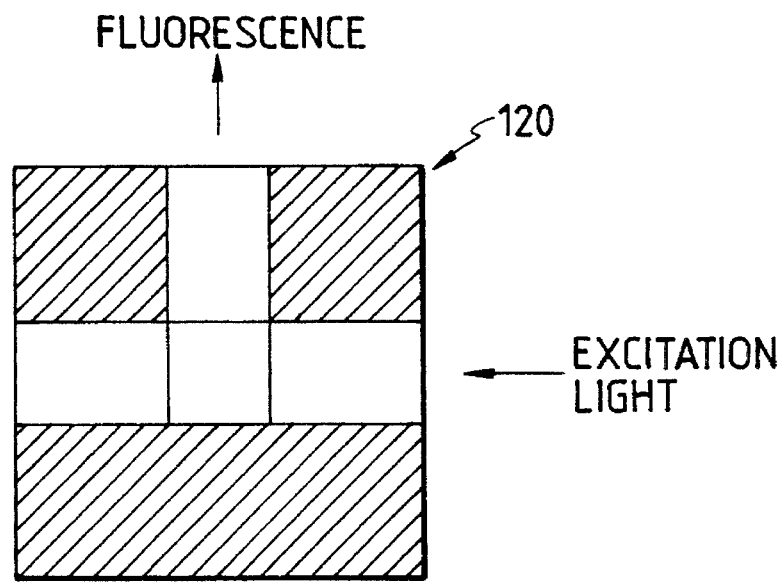
FIG. 8 is a view showing another embodiment of the sample cell.

FIG. 8 shows a modified specimen cell. Compared with the sample cell shown in FIG. 2, one edge causing the light scattering as shown in FIG. 6 is eliminated and thus, the light scattering can be halved. In addition, since portions to be adhered are less, the manufacturing cost is also low.

Figure 9:
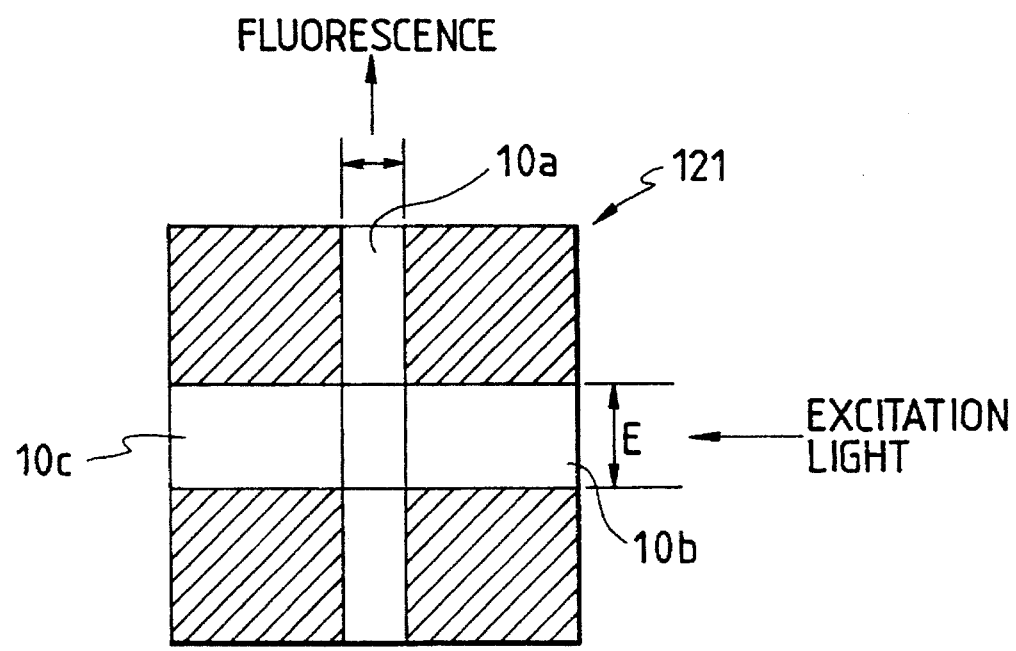
FIG. 9 is a view showing an example of forming a sample cell suitable for obtaining a narrow spectrum band.

FIG. 9 shows an example of forming the sample cell 121 when the narrow spectrum band of the fluorescence side monochromator is required. As shown in this embodiment, the slit can be reduced in width while the sample chamber remains the same in capacity if the fluorescence output port 10a is reduced in width, while the excitation light side port 10b and the reference light output port 10c are increased in width, respectively.

Figure 10:
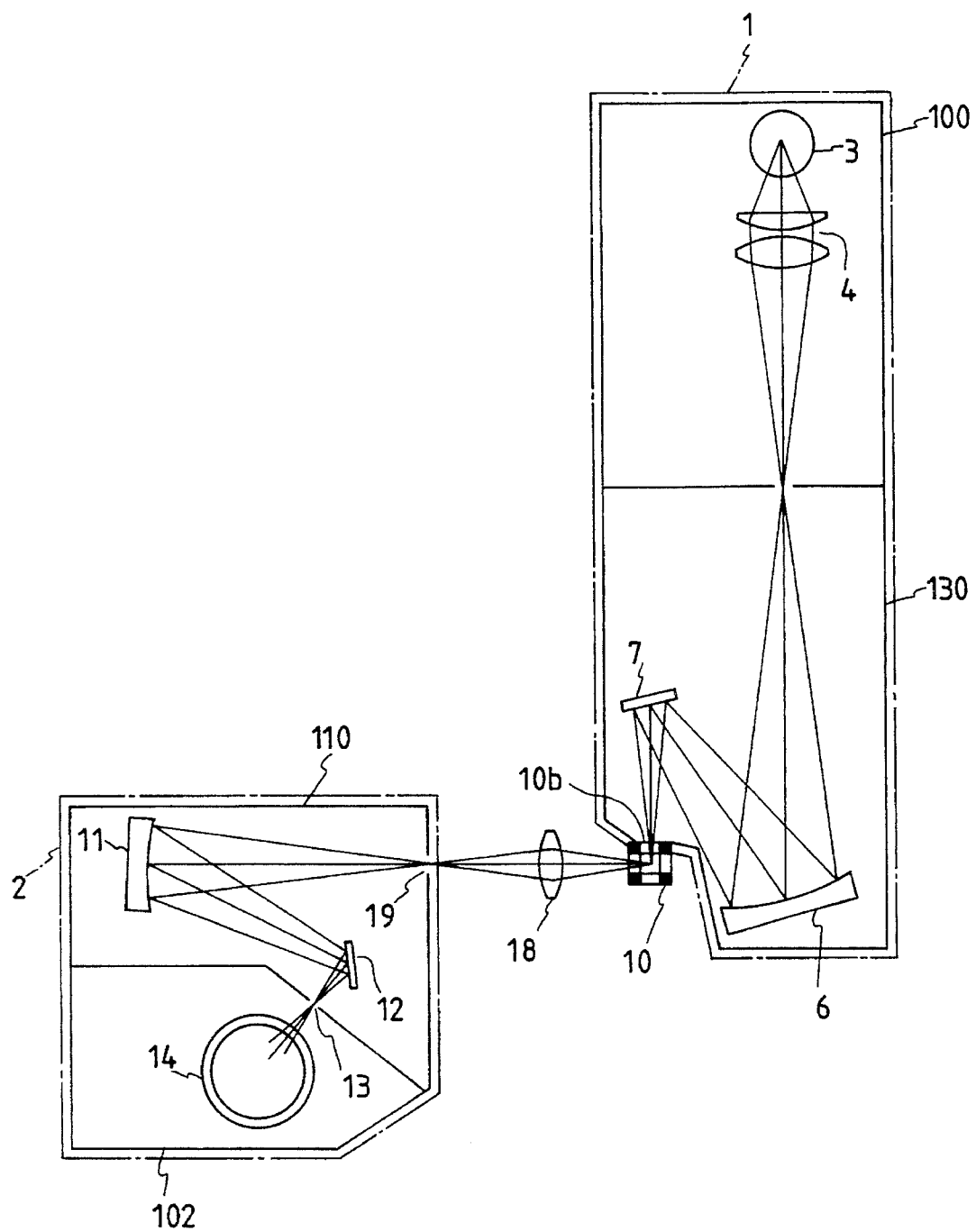
FIG. 10 is a view showing a second embodiment in which the excitation light port is arranged at a position corresponding to the excitation light side entrance slit.

FIG. 10 shows a second embodiment of this invention. In this embodiment, the excitation light port 10b of the sample chamber 10 is provided at a position corresponding to the exit slit of the monochromator section 103 of the excitation side basic optical system 1 of the spectrofluorometer.

Just like the embodiment shown in FIG. 1, the light emitted from the light source 3 arranged in the light source section 100 in the excitation light side basic optical system 1 is condensed by the condensing lens 4 arranged in the light source section 100. The light then goes through the entrance slit 5 and dispersed by the concave diffraction grating 6 in the monochromator section 130.

The dispersed monochromatic light goes through the mirror 7 and the excitation light side port 10b of the sample cell 10 and is directed to the sample chamber 300. In this embodiment, the excitation light side port 10b of the specimen chamber 10 is provided at a position corresponding to the exit slit of the monochromator, so the excitation light side port 10b is used as a pseudo exit slit.

This configuration allows the excitation light side port 10b to work just like the exit slit in the prior art.

In other words, since the member that can work just like an exit slit is provided at the condensing position of the concave diffraction grating 6, the exit slit used in the conventional monochromator can be eliminated. And since the excitation light side port 10b provided between the light-shielding members 200 is works as a pseudo slit, the exit slit in the prior art can be eliminated. As a result, the light path between the exit slit 8 in the prior art and the sample cell 10 can be omitted, as well as the condensing lens 18 and the entrance slit 19 in the prior art can also be eliminated. Also in this embodiment, the same effect as that of the embodiment shown in FIG. 1 can be obtained in the excitation side basic optical system.

Figure 11:
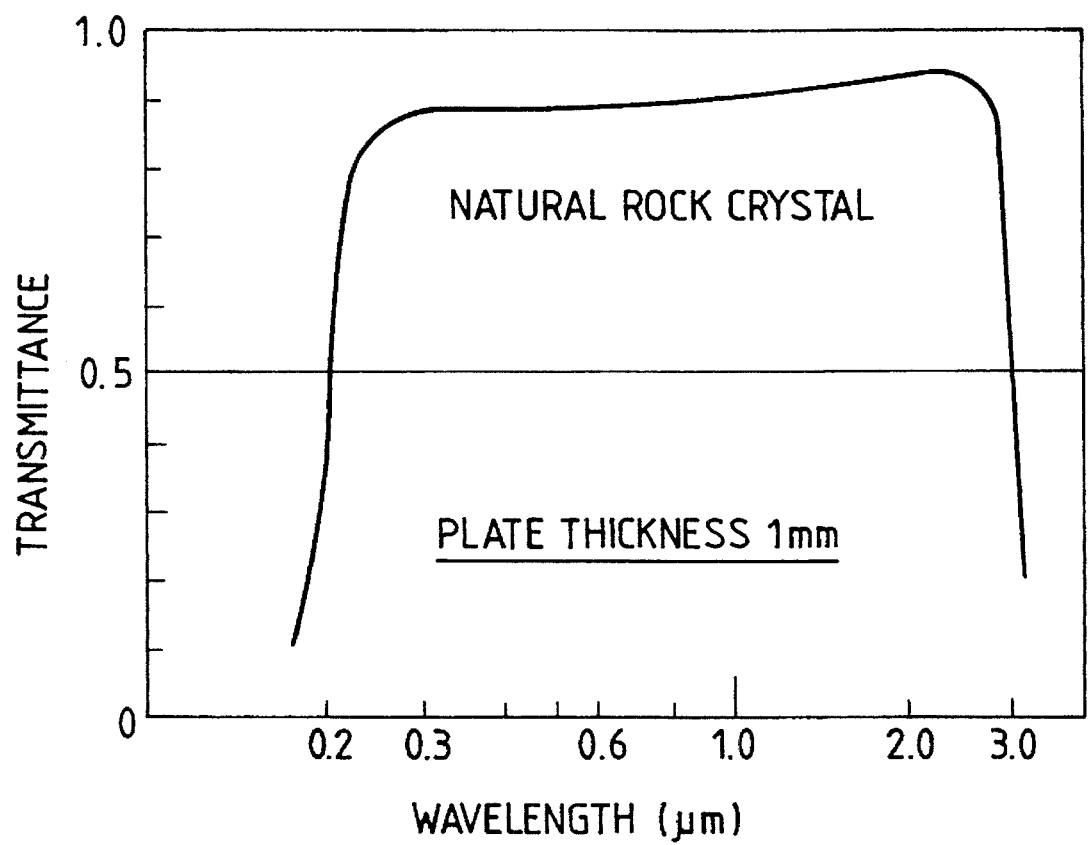
FIG. 11 is a view showing the transmission curve of a general lens.

The material of a general lens gives a transmission curve as shown in FIG. 11. For example, when a short wavelength excitation light of 240 nm or under is used for measurement, the light loss can be reduced extremely when no lens is used.

Figure 12:
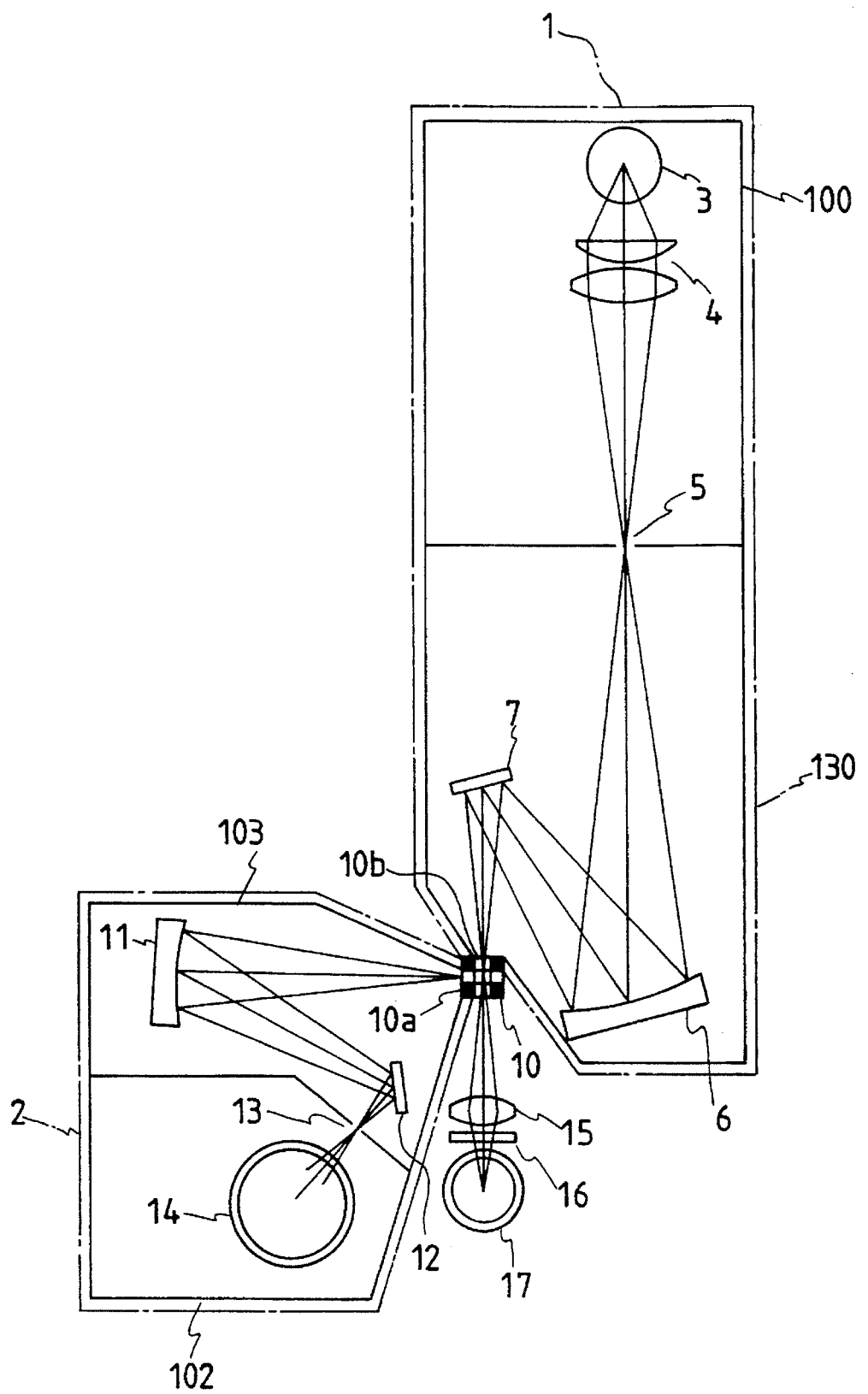
FIG. 12 is a view showing an optical system in a third embodiment.

FIG. 12 shows a third embodiment in which the embodiment shown in FIG. 1 and the embodiment shown in FIG. 10 are combined.

In other words, both the optical systems and the sample cell are arranged so that the excitation light side port 10b is provided at a position corresponding to the exit slit of the monochromator 130 of the excitation light side basic optical system 1, as well as the fluorescence output port 10a is provided at a position corresponding to the entrance slit of the monochromator 103 of the fluorescence side basic optical system 2. Thus, the effects of both the embodiments shown in FIGS. 1 and 10 can be obtained. The number of the optical elements shown in this embodiment is the smallest of those shown in the embodiments. This makes it possible to eliminate the light loss to be caused by the convergence system provided on this side of the sample cell.

In the embodiments mentioned above, the convergence means in the monochromator may be the combination of a concave diffraction grating and a flat mirror or the combination of a concave mirror and a flat diffraction grating. The gratings and mirrors can be combined freely in another way.

Figure 13:
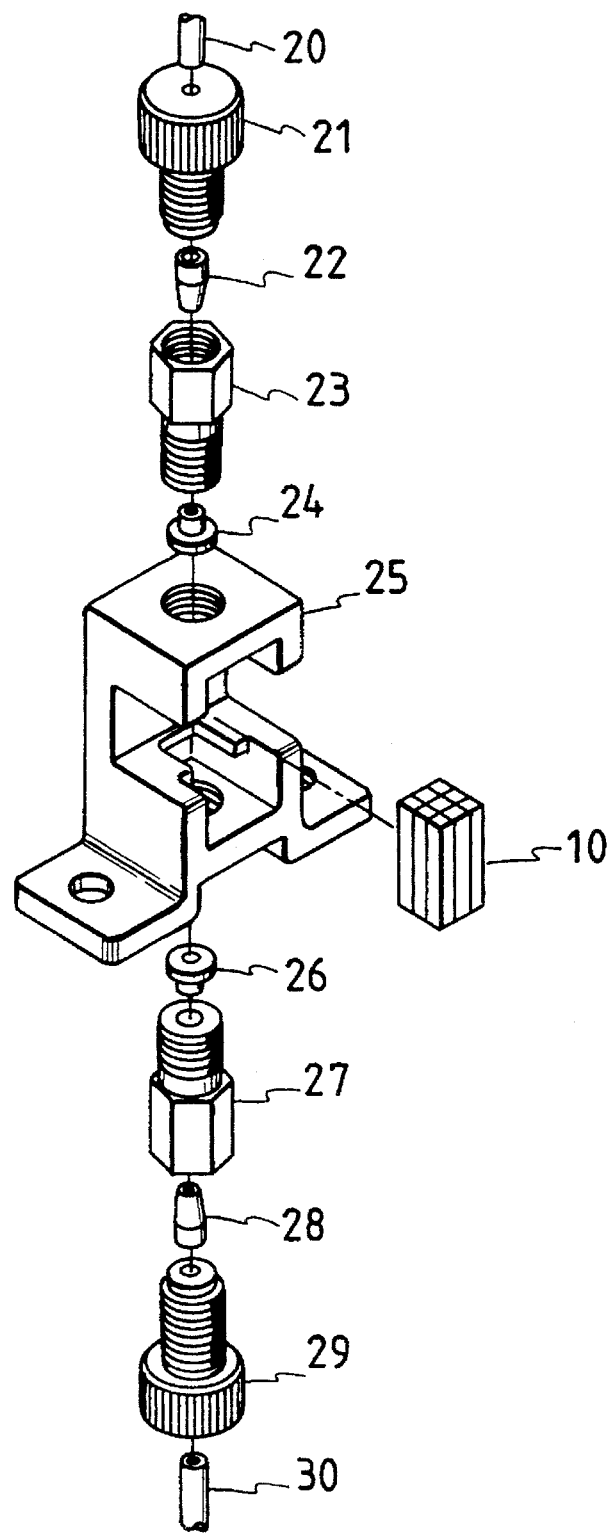
FIG. 13 is an enlarged perspective view of the detailed specimen cell configuration.

FIG. 13 shows a disassembled perspective view of the specimen cell configuration used in the embodiments shown in FIGS. 1 through 3. The sample cell 10 is placed in a cell holder 25. The sample cell placed thus is pressed and fixed in the cell holder 25 by setscrews 23 and 27 via spacers 24 and 26 from both top and bottom. Tubes 20 and 30 are connected by means of the setscrews 23 and 27 in association with members 22 and 28 and fixing screws 21 and 29. A flow path is formed such way between the tubes 30 and 20 through the specimen cell 10. Liquid is fed from a separation column into this flow path so that the flow path can be used as a liquid chromatograph detector.

The light path for measuring in the spectrofluorometer excitation light side basic optical system and/or in the fluorescence side optical system can be shortened. This makes it possible to reduce the scattering and loss of the measuring light and improve the sensitivity and measuring accuracy of the measuring system.

As seen from the foregoing, in the excitation light side basic optical system and/or in the fluorescence side basic optical system of the spectrofluorometer, the measurement optical paths are reduced and thus the measurement is carried out with high sensitivity and precision because the light loss is decreased. In addition, the condensing lenses can be eliminated from the fluorescence side basic optical system and the excitation side basic optical system. With this, the light loss can be reduced, so that the sensitivity of the measuring system can be improved.

What is claimed is:

1. A spectrofluorometer comprising:
   a) a sample cell including:
      i) a sample chamber to hold a sample;
      ii) an excitation light port to direct excitation light to said sample chamber;
      iii) a fluorescence output port to derive fluorescence emitted from the sample in the said sample chamber; and
      iv) light-shielding members arranged to sandwich said excitation light port and said fluorescent output port therebetween;
   b) an excitation side monochronometer to derive the excitation light to be directed to said sample;
   c) a fluorescence side monochronometer to analyze the fluorescence from said sample cell;
   d) a fluorescence detector to detect the fluorescence from said fluorescence side monochronometer; and
   e) the output port of said sample chamber forming an entrance slit for said fluorescence side monochronometer.

2. A spectrofluorometer described in claim 1, further comprising a transmitted light detector to receive the excitation light that passes through said excitation light port and the sample, and comparing means to compare an output of said fluorescence detector with an output of said transmitted light detector.

3. A spectrofluorometer described in claim 1, wherein a convergence position of the excitation light to be made incident on said sample chamber is set further than the center of said sample chamber when viewing from the light source side.

4. A spectrofluorometer described in claim 1, wherein said sample cell further comprises a transmitted light output port provided in the forward direction of the excitation light passing through said sample cell.

5. A spectrofluorometer described in claim 1 wherein said sample cell is arranged so that an output of said fluorescence output port is provided at a convergence position on a light path of light-dispersing means provided in said fluorescence side monochronometer.

6. A spectrofluorometer comprising:
a) a sample cell including:
  i) a sample chamber to hold a sample;
  ii) an excitation light port to direct excitation light to said sample chamber;
  iii) a fluorescence output port to derive fluorescence emitted from the sample in the said sample chamber; and
  iv) light-shielding members arranged to sandwich said excitation light port and said fluorescent output port therebetween;
b) an excitation side monochronometer to derive the excitation light to be directed to said sample;
c) a fluorescence side monochronometer to analyze the fluorescence from said sample cell;
d) a fluorescence detector to detect the fluorescence from said fluorescence side monochronometer; and
e) the excitation light port of said sample chamber forming an exit slit for said excitation monochronometer.

7. A spectrofluorometer described in claim 6, further comprising a transmitted light detector to receive the excitation light that passes through said excitation light port and the sample, and comparing means to compare an output of said fluorescence detector with an output of said transmitted light detector.

8. A spectrofluorometer described in claim 6, wherein a convergence position of the excitation light to be directed to the said sample chamber is provided further than the center of said specimen chamber when viewing from the light source side.

9. A spectrofluorometer described in claims 6, wherein said sample cell further comprises a transmitted light output port provided in the forward direction of the excitation light passing through said sample cell.

10. A spectrofluorometer described in claim 6 wherein said sample cell is arranged so that said excitation light port is provided at a convergence position on a light path of light-dispersing means provided in said excitation light side monochronometer.

11. A spectrofluorometer comprising:
a) a sample cell including:
  i) a sample chamber to hold a sample;
  ii) an excitation light port to direct excitation light to said sample chamber;
  iii) a fluorescence output port to derive fluorescence emitted from the sample in the said sample chamber; and
  iv) light-shielding members arranged to sandwich said excitation light port and said fluorescent output port therebetween;
b) an excitation side monochronometer to derive the excitation light to be directed to said sample;
c) a fluorescence side monochronometer to analyze the fluorescence from said sample cell;
d) a fluorescence detector to detect the fluorescence from said fluorescence side monochronometer;
e) the output port of said sample chamber forming an entrance slit for said fluorescence side monochronometer; and
f) the excitation light port of said sample chamber forming an exit slit for said excitation monochronometer.

12. A spectrofluorometer described in claim 11, further comprising a transmitted light detector to receive the excitation light that passes through said excitation light port and the sample, and comparing means to compare an output of said fluorescence detector with an output of said transmitted light detector.

13. A spectrofluorometer described in claim 11, wherein a convergence position of the excitation light to be directed to said sample chamber is set further than the center of said sample chamber when viewing from the light source side.

14. A spectrofluorometer described in claim 11, wherein said sample cell further comprises a transmitted light output port provided in the forward direction on the excitation light passing through said sample cell.

15. A spectrofluorometer described in claim 11 wherein said excitation light port is provided at a convergence position on a light path of a light-dispersing means provided in said excitation light side monochronometer and said fluorescence output port is provided at a convergence position on a light path of diffraction means provided in said fluorescence-side monochronometer.

16. A spectrofluorometer described in claim 11 wherein said sample cell is provided with light-transmitting members in addition to said light-shielding members, each of said excitation light port and said fluorescent output port being made of one of said light-transmitting members so as to function as a slit formed between of said light-shielding members, and said sample chamber being enclosed by said excitation light port, said fluorescent output port and said light-shielding member.

17. A spectrofluorometer described in claim 11 wherein said sample cell is a rectangular parallelepiped in form and is hollow through from top to bottom in the longitudinal direction of said rectangular parallelepiped, said light-shielding members being arranged on the four corners of said rectangular parallelepiped in the longitudinal direction thereof with transparent members arranged between said light-shielding members.

\* \* \* \* \*

UNITED STATES PATENT AND TRADEMARK OFFICE
CERTIFICATE OF CORRECTION

PATENT NO. : 5,500,536
DATED : March 19, 1996
INVENTOR(S) : Taro Nogami et al.

It is certified that error appears in the above-indentified patent and that said Letters Patent is hereby corrected as shown below:

Column 7, line 32, change "claims 6" to --claim 6--.

Signed and Sealed this

Thirteenth Day of August, 1996

Attest:

BRUCE LEHMAN

*Attesting Officer*     *Commissioner of Patents and Trademarks*